US011647952B2

(12) United States Patent
Hassan-Ali et al.

(10) Patent No.: US 11,647,952 B2
(45) Date of Patent: May 16, 2023

(54) GARMENT INTEGRATED DRY ELECTRODE FOR VITAL SIGNAL AND ELECTROMYOGRAPHY SENSING

(71) Applicant: Flex Ltd., Singapore (SG)

(72) Inventors: Mudhafar Hassan-Ali, Menlo Park, CA (US); Phuocan N. Nguyen, Milpitas, CA (US); Srinivasa Varadan Rajagopalan, Milpitas, CA (US); Jeffrey B. Cross, Aptos, CA (US); Anthony Joseph Piazza, San Jose, CA (US); Mark A. Bergman, Redwood City, CA (US)

(73) Assignee: Flex Ltd., Singapore (SG)

( * ) Notice: Subject to any disclaimer, the term of this patent is extended or adjusted under 35 U.S.C. 154(b) by 492 days.

(21) Appl. No.: 16/427,724

(22) Filed: May 31, 2019

(65) Prior Publication Data
US 2020/0037955 A1 Feb. 6, 2020

Related U.S. Application Data

(60) Provisional application No. 62/713,079, filed on Aug. 1, 2018, provisional application No. 62/713,131, filed on Aug. 1, 2018.

(51) Int. Cl.
*A61B 5/00* (2006.01)
*A61B 5/296* (2021.01)
(Continued)

(52) U.S. Cl.
CPC ............ *A61B 5/6804* (2013.01); *A41D 1/002* (2013.01); *A41D 13/02* (2013.01);
(Continued)

(58) Field of Classification Search
CPC ....... A61B 5/6804; A61B 5/296; A61B 5/282; A61B 5/25; A61B 5/0059; A61B 5/01;
(Continued)

(56) References Cited

U.S. PATENT DOCUMENTS

2002/0032386 A1 3/2002 Sackner et al.
2005/0261562 A1 11/2005 Zhou et al.
(Continued)

FOREIGN PATENT DOCUMENTS

| CN | 104883968 | 9/2015 |
| WO | WO 2017/075703 | 5/2017 |
| WO | WO 2017/189367 | 11/2017 |

OTHER PUBLICATIONS

International Report on Patentability for International (PCT) Patent Application No. PCT/US2019/034830, dated Feb. 11, 2021 12 pages.
(Continued)

*Primary Examiner* — Adam Z Minchella
(74) *Attorney, Agent, or Firm* — Sheridan Ross P.C.

(57) ABSTRACT

Embodiments of the disclosure provide systems and methods for wearable dry electrodes for collecting biometric information. According to one embodiment, a dry electrode bio-sensor can comprise one or more conductive pads comprising electrodes of the dry electrode bio-sensor and one or more connectivity traces coupled with each of the one or more conductive pads. The connectivity traces can provide electrical connections for one or more of power to the one or more conductive pads or signals comprising biometric information from the one or more conductive pads. A backing can be coupled with and can retain the one or more conductive pads and the one or more connectivity traces. The dry electrode bio-sensor can comprise an electrocardiography (ECG) sensor, a respiration sensor, a PhotoPlethys-
(Continued)

moGram (PPG) sensor, a temperature sensor, an electromyography (EMG) sensor, or another biometric sensor.

16 Claims, 9 Drawing Sheets

(51) Int. Cl.

| | | |
|---|---|---|
| *G16H 50/30* | (2018.01) | |
| *A41D 13/12* | (2006.01) | |
| *A61B 5/08* | (2006.01) | |
| *A61B 5/01* | (2006.01) | |
| *A41D 1/00* | (2018.01) | |
| *A41D 13/02* | (2006.01) | |
| *A61B 5/25* | (2021.01) | |
| *A61B 5/282* | (2021.01) | |

(52) U.S. Cl.
CPC ........ *A41D 13/1281* (2013.01); *A61B 5/0059* (2013.01); *A61B 5/01* (2013.01); *A61B 5/0809* (2013.01); *A61B 5/0816* (2013.01); *A61B 5/25* (2021.01); *A61B 5/282* (2021.01); *A61B 5/296* (2021.01); *A61B 5/6843* (2013.01); *G16H 50/30* (2018.01); *A61B 2562/0209* (2013.01)

(58) Field of Classification Search
CPC ... A61B 5/0809; A61B 5/0816; A61B 5/6843; A61B 2562/0209; G16H 50/30; A41D 1/002; A41D 13/02; A41D 13/1281
See application file for complete search history.

(56) References Cited

U.S. PATENT DOCUMENTS

| | | |
|---|---|---|
| 2006/0124193 A1 | 6/2006 | Orr et al. |
| 2007/0169533 A1 | 7/2007 | Shah et al. |
| 2007/0293781 A1 | 12/2007 | Sims et al. |
| 2010/0185068 A1 | 7/2010 | Park et al. |
| 2012/0136231 A1 | 5/2012 | Markel |
| 2012/0246795 A1 | 10/2012 | Scheffler et al. |
| 2014/0070957 A1 | 3/2014 | Longinotti-Buitoni |
| 2014/0073895 A1* | 3/2014 | Freeman .............. A61B 5/6823 600/382 |
| 2014/0114166 A1* | 4/2014 | Baxi ........................ A61B 5/25 600/384 |
| 2014/0249430 A1 | 9/2014 | Sims et al. |
| 2014/0285216 A1 | 9/2014 | Cuddihy et al. |
| 2015/0148619 A1 | 5/2015 | Berg et al. |
| 2016/0103985 A1 | 4/2016 | Shim et al. |
| 2017/0258402 A1* | 9/2017 | Acquista .............. A61B 5/6833 |
| 2018/0067516 A1* | 3/2018 | Longinotti-Buitoni ..................... G16H 40/67 |
| 2018/0090449 A1 | 3/2018 | Jeong et al. |
| 2018/0184735 A1* | 7/2018 | Longinotti-Buitoni ..................... A63B 24/0062 |
| 2019/0246993 A1 | 8/2019 | Gupta et al. |
| 2020/0138374 A1* | 5/2020 | Kitazawa ................. A61B 5/25 |

OTHER PUBLICATIONS

International Report on Patentability for International (PCT) Patent Application No. PCT/US2019/034833, dated Feb. 11, 2021 8 pages.
Official Action for U.S. Appl. No. 16/427,713, dated Mar. 4, 2021 18 pages.
U.S. Appl. No. 16/427,713, filed May 31, 2019, Hassan-Ali et al.
International Search Report and Written Opinion for International (PCT) Patent Application No. PCT/US2019/034830, dated Aug. 15, 2019 13 pages.
International Search Report and Written Opinion for International (PCT) Patent Application No. PCT/US2019/034833, dated Aug. 9, 2019 9 pages.
Final Action for U.S. Appl. No. 16/427,713, dated Sep. 16, 2021 21 pages.
Official Action for U.S. Appl. No. 16/427,713, dated Jan. 6, 2022 21 pages.
Official Action (with English translation) for Chinese Patent Application No. 201980051011.3, dated Jun. 15, 2022 24 pages.
Final Action for U.S. Appl. No. 16/427,713, dated Jun. 23, 2022 21 pages.

* cited by examiner

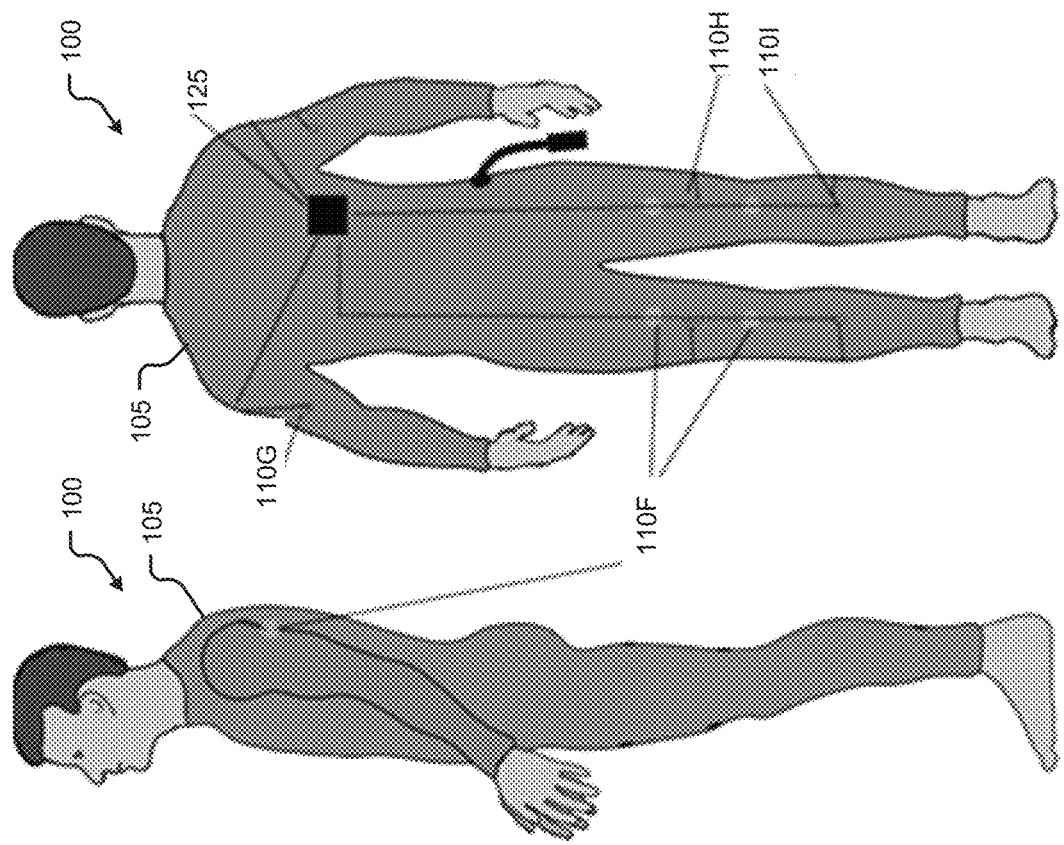
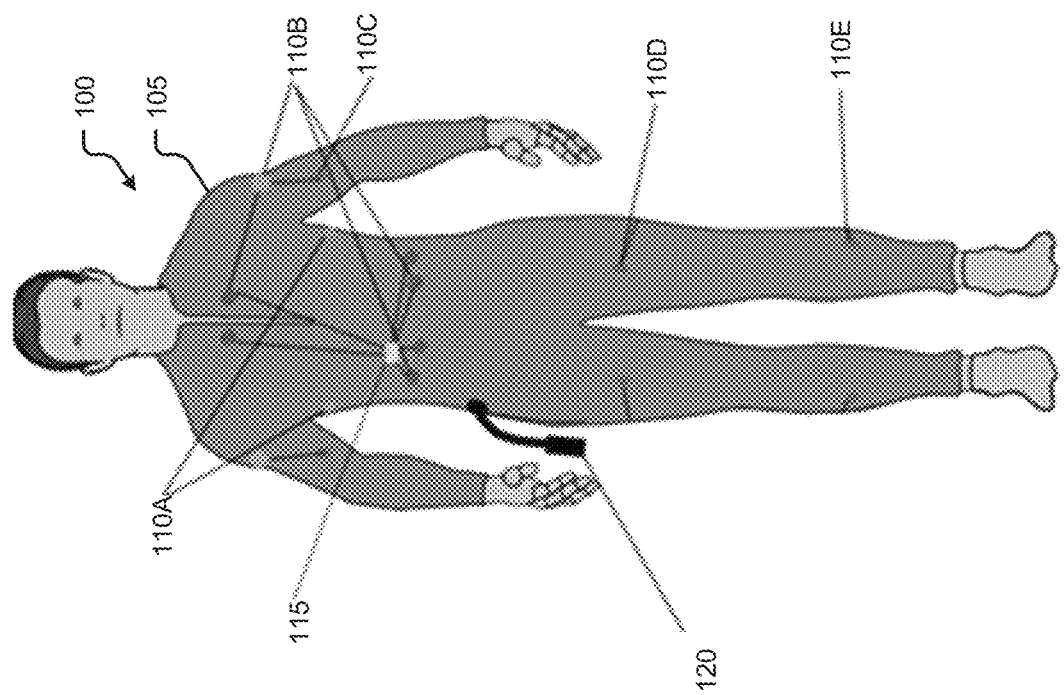
Fig. 1A  Fig. 1B  Fig. 1C

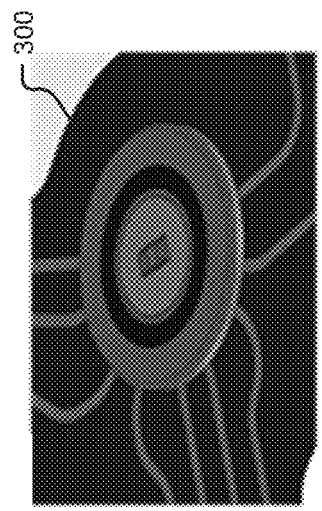
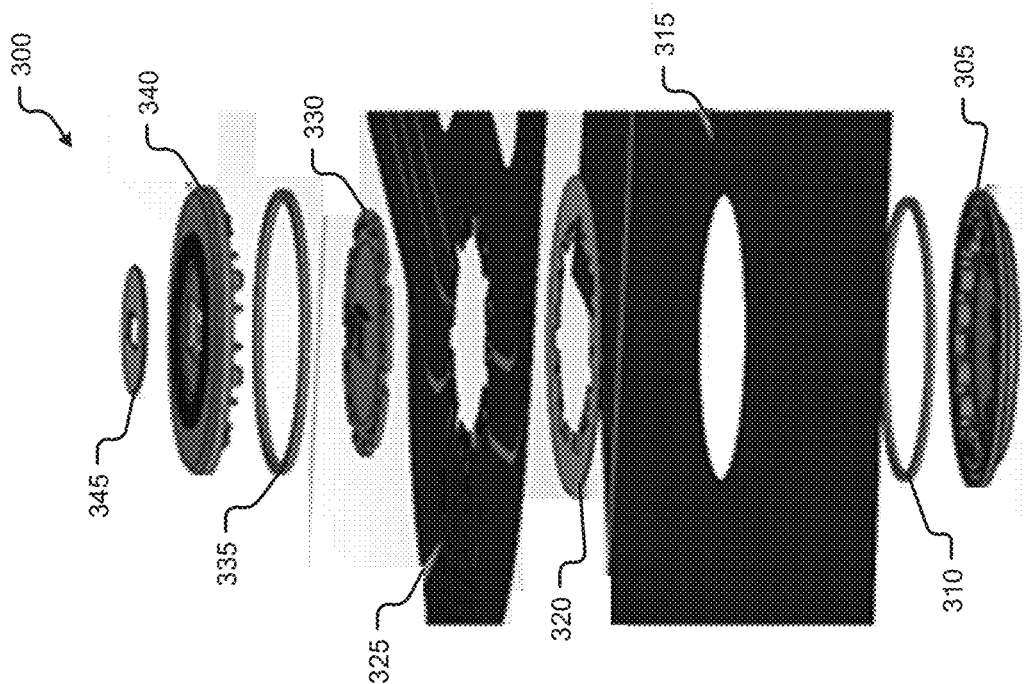

GARMENT INTEGRATED DRY ELECTRODE FOR VITAL SIGNAL AND ELECTROMYOGRAPHY SENSING

CROSS REFERENCE TO RELATED APPLICATION

The present application claims the benefits of and priority, under 35 U.S.C. § 119(e), to U.S. Provisional Application No. 62/713,131 filed Aug. 1, 2018 by Mudhafar et al. and entitled "Bio-Sensing Integrated Garment" and U.S. Provisional Application No. 62/713,079 filed Aug. 1, 2018 by Mudhafar et. al and entitled "Garment Integrated Dry Electrode for Vital Signal and Electromyography Sensing." The entire disclosure of each application listed above is incorporated herein by reference, in its entirety, for all that it teaches and for all purposes.

STATEMENT REGARDING FEDERALLY SPONSORED RESEARCH OR DEVELOPMENT

This invention was made with U.S. Government support under a Development Agreement supported by an award by the Air Force Research Laboratory. The U.S. Government has certain rights in the invention.

FIELD OF THE DISCLOSURE

Embodiments of the present disclosure relate generally to methods and systems for collecting biometric information and more particularly to wearable dry electrodes for collecting biometric information.

BACKGROUND

Sensing of vital signs, e.g., heart rate, respiration, temperature, etc., and electromyography, i.e., measurement of muscular activity, and other biometric monitoring are important in a variety of applications ranging from health monitoring of medical patients to performance monitoring of athletes and a combination of performance and health monitoring of military personnel, astronauts, etc. Typically, sensors for performing such monitoring are applied to the monitored person individually at various locations depending on the information monitored. This can be time consuming and tedious if measuring multiple different biometric information. Additionally, such sensors are prone to slippage or dislocation, are susceptible to contamination by dirt and moisture, and may be limiting of the motion of the wearer when the wearer is active. Hence, there is a need in the art for improved systems and methods for collecting biometric information.

BRIEF SUMMARY

Embodiments of the disclosure provide systems and methods for wearable dry electrodes for collecting biometric information. According to one embodiment, a dry electrode bio-sensor can comprise one or more conductive pads comprising electrodes of the dry electrode bio-sensor and one or more connectivity traces coupled with each of the one or more conductive pads. The connectivity traces can provide electrical connections for one or more of power to the one or more conductive pads or signals comprising biometric information from the one or more conductive pads. A backing can be coupled with and can retain the one or more conductive pads and the one or more connectivity traces.

The dry electrode bio-sensor can comprise an electrocardiography (ECG) sensor, a respiration sensor, a PhotoPlethysmoGram (PPG) sensor, a temperature sensor, an electromyography (EMG) sensor, or another biometric sensor.

The one or more conductive pads and the one or more connectivity traces can be printed in stretchable and washable conductive ink. In some cases, the one or more conductive pads and one or more connectivity traces can be printed on a stretchable and washable substrate. A surface of each of the one or more conductive pads placed against a wearer's skin when the dry electrode bio-sensor is in use can be textured.

A standoff can be disposed on a side of the backing opposite from the one or more conductive pads, the standoff transferring pressure to the one or more conductive pads when the conductive pads are applied to a skin of a wearer of the dry-electrode bio-sensor. The standoff can be constructed of a flexible material. The pressure transferred by the standoff to the one or more conductive pads can be applied by a compressive textile. The shape of the standoff on a portion adjacent to the compressive textile can have a more curvature than a portion adjacent to the one or more conductive pads.

A bio-sensing garment for collecting biometric information from a wearer of the garment, the garment comprising a fabric layer forming the garment and a plurality of dry electrode bio-sensors integrated into the fabric layer. Each dry-electrode bio-sensor can comprise one or more conductive pads comprising electrodes of the dry electrode bio-sensor, one or more connectivity traces coupled with each of the one or more conductive pads, the connectivity traces providing electrical connections for one or more of power to the one or more conductive pads or signals comprising biometric information from the one or more conductive pads, and a backing coupled with and retaining the one or more conductive pads and the one or more connectivity traces. A connectivity layer can be integrated into the fabric layer and can comprise one or more signal conductors coupled with one or more of the connectivity traces of each dry electrode bio-sensors and one or more power conductors coupled with one or more of the connectivity traces of each dry electrode bio-sensors. A power source can be coupled with each of the power conductors and can provide, via the power conductors of the connectivity layer, electrical power to each of the plurality of dry electrode bio-sensors. A signal monitor can be coupled with the connectivity layer and can receive, via the signal conductors of the connectivity layer, a signal comprising biometric information from each of the plurality of dry electrode bio-sensors. A gateway can be coupled with the signal monitor. The gateway can receive the biometric information from the signal monitor and providing the biometric information to an external computer system.

The one or more conductive pads and the one or more connectivity traces of the dry electrode bio-sensors can be printed in stretchable and washable conductive ink. In some cases, the one or more conductive pads and one or more connectivity traces can be printed on a stretchable and washable substrate. A surface of each of the one or more conductive pads placed against a wearer's skin when the dry electrode bio-sensor is in use can be textured. A standoff can be disposed on a side of the backing opposite from the one or more conductive pads. The standoff can transfer pressure to the one or more conductive pads when the conductive pads are applied to a skin of a wearer of the dry-electrode bio-sensor. The standoff can be constructed of a flexible material and the pressure transferred by the standoff to the one or more conductive pads can be applied by the fabric layer. A shape of the standoff on a portion adjacent to the compressive textile can have a more curvature than a portion adjacent to the one or more conductive pads.

BRIEF DESCRIPTION OF THE DRAWINGS

FIGS. 1A-1C are diagram illustrating various views of a bio-sensing integrated garment according to one embodiment of the present disclosure.

FIGS. 3A and 3B illustrate various views of an exemplary biometric signal monitor according to one embodiment of the present disclosure.

Figure 2A:
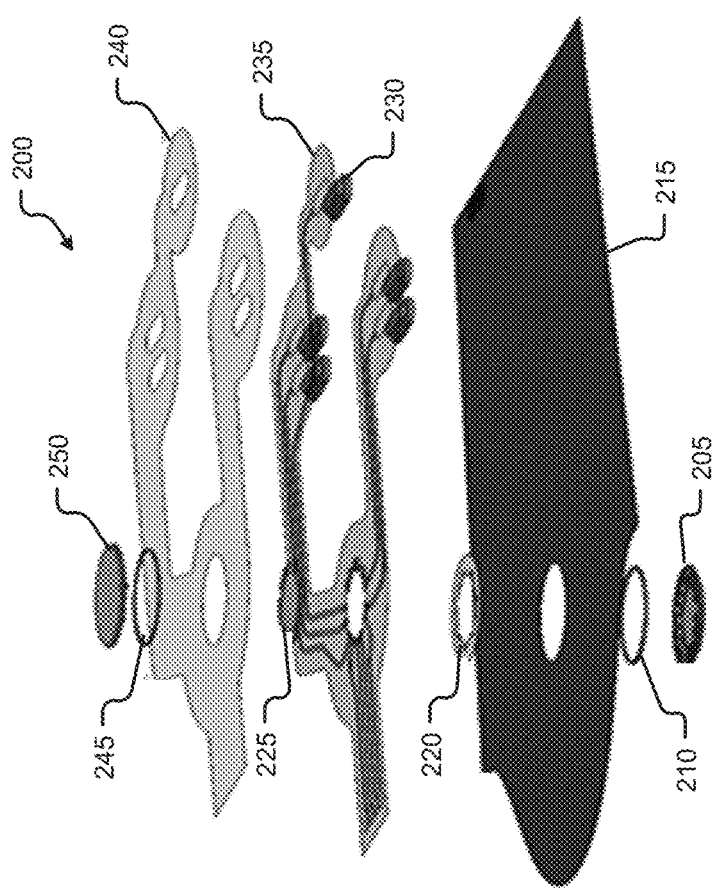
FIGS. 2A and 2B illustrate various views of an exemplary biometric sensor according to one embodiment of the present disclosure.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

In the following description, for the purposes of explanation, numerous specific details are set forth in order to provide a thorough understanding of various embodiments disclosed herein. It will be apparent, however, to one skilled in the art that various embodiments of the present disclosure may be practiced without some of these specific details. The ensuing description provides exemplary embodiments only, and is not intended to limit the scope or applicability of the disclosure. Furthermore, to avoid unnecessarily obscuring the present disclosure, the preceding description omits a number of known structures and devices. This omission is not to be construed as a limitation of the scopes of the claims. Rather, the ensuing description of the exemplary embodiments will provide those skilled in the art with an enabling description for implementing an exemplary embodiment. It should however be appreciated that the present disclosure may be practiced in a variety of ways beyond the specific detail set forth herein.

While the exemplary aspects, embodiments, and/or configurations illustrated herein show the various components of the system collocated, certain components of the system can be located remotely, at distant portions of a distributed network, such as a Local-Area Network (LAN) and/or Wide-Area Network (WAN) such as the Internet, or within a dedicated system. Thus, it should be appreciated, that the components of the system can be combined in to one or more devices or collocated on a particular node of a distributed network, such as an analog and/or digital telecommunications network, a packet-switch network, or a circuit-switched network. It will be appreciated from the following description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

As used herein, the phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, Non-Volatile Random-Access Memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a Compact Disk Read-Only Memory (CD-ROM), any other optical medium, punch cards, paper tape, any other physical medium with patterns of holes, a Random-Access Memory (RAM), a Programmable Read-Only Memory (PROM), and Erasable Programmable Read-Only Memory (EPROM), a Flash-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

A "computer readable signal" medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, Radio Frequency (RF), etc., or any suitable combination of the foregoing.

The terms "determine," "calculate," and "compute," and variations thereof, as used herein, are used interchangeably and include any type of methodology, process, mathematical operation or technique.

It shall be understood that the term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the disclosure, brief description of the drawings, detailed description, abstract, and claims themselves.

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Any combination of one or more computer readable medium(s) may be utilized. The computer readable medium may be a computer readable signal medium or a computer readable storage medium.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as Programmable Logic Device (PLD), Programmable Logic Array (PLA), Field Programmable Gate Array (FPGA), Programmable Array Logic (PAL), special purpose computer, any comparable means, or the like. In general, any device(s) or means capable of implementing the methodology illustrated herein can be used to implement the various aspects of this disclosure. Exemplary hardware that can be used for the disclosed embodiments, configurations, and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or Very Large-Scale Integration (VLSI) design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or Common Gateway Interface (CGI) script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

Various additional details of embodiments of the present disclosure will be described below with reference to the figures. While the flowcharts will be discussed and illustrated in relation to a particular sequence of events, it should be appreciated that changes, additions, and omissions to this sequence can occur without materially affecting the operation of the disclosed embodiments, configuration, and aspects.

Embodiments of the disclosure provide systems and methods for a garment including integrated sensors for collecting biometric information. Generally speaking and as will be described in greater detail below, to monitor health and muscular activities, a garment equipped with bio-sensors could be worn by a person whose health requires a continuous monitoring. Such garment could be equipped with bio-sensors that monitors vital signals such as ECG, respiration, PPG, blood pressure, core body temperature, as well as muscular activities like EMG. These sensors can be located within the garment and on the body of the wearer of the garment to monitor electrical signals as well as by other sensing means like optically or thermally. The signals generated by these sensors can be gathered and processed by electronic circuits that are interconnected via a web of connectivity layer integrated in the garment. These interconnected sensors and circuits can be so integrated into the garment that the interference with the person's normal activities is minimal. Electrical power for the bio-sensing system could be provided by a portable source within, on, or near the garment or by using energy harvesting means similarly situated within, on, or near the garment. The monitoring data can be transmitted on wire or wireless communications connection to a computing node for further analysis and alarm generation as appropriate.

FIGS. 1A-1C are diagram illustrating various views of a bio-sensing integrated garment according to one embodiment of the present disclosure. More specifically, FIG. 1A illustrates a front view of a bio-sensing integrated garment 100 as described herein. As illustrated in this example, the bio-sensing integrated garment 100 can comprise a fabric layer 105 forming a suit substantially covering the torso, arms, and legs of the wearer. A number of sensors 110A-110E can be seen in this view. These sensors 110A-110E can be connected with a connectivity layer 115 of the garment. The sensors 110A-110E and other elements of the garment as will be described can be by using conductive ink printed in a flexible and stretchable substrate such as TPU bonded to the fabric layer 105 of the garment 100. The sensors 110A-110E can include, but are not limited to, an ECG sensor which can consist of electrodes, printed connectivity traces, electronic circuits for digitization of the ECG signal, a respiration sensor which can consist of electrodes for bio-impedance measurement, electronics circuits, printed connectivity traces, a PPG sensor which can consist of an optical sensor (itself consists of a number of LEDs and Photo Detectors), and electronic circuit that drives the optical sensor, a temperature sensor and printed connectivity traces, an EMG sensor which can consist of pairs of electrodes, printed connectivity traces, and electronic circuit for digitization of the analog signal, and/or other sensors for collecting biometric information from the wearer of the bio-sensing integrated garment 100.

FIG. 1B illustrates a side view of the bio-sensing integrated garment 100 while FIG. 1C illustrates a back view of the bio-sensing integrated garment 100. In each of these views, additional sensors 110F-110I can be seen in different locations for measuring different biometric information. Additionally, a signal monitor 125 can be seen. Generally speaking and as will be described in greater detail below, the signal monitor 125 can receive the biometric information from the various sensors 110A-110I and provide that information to an external computer system (not shown here) for monitoring. In some cases, the bio-sensing integrated garment 100 may include one or more electrical connectors that may provide wired access to the external computer system and/or provide electrical power to the sensors 110A-110I, signal monitor and other elements of the bio-sensing integrated garment 100. Additionally, or alternatively, the signal monitor 125 of the bio-sensing integrated garment 100 may utilize one or more wireless communications transmitters to provide the biometric information to the external computer system.

The electronic circuits for the sensors 110A-110I can be interconnected via the connectivity layer (not shown here) which can comprise a web of traces printed on a stretchable and bio-compatible substrate, such as TPU, using conductive ink. This substrate can be bound to the fabric layer of the bio-sensing integrated garment 100. These traces could be made in different conductive ink with different geometries including straight shapes as well as meander shapes so as to achieve the minimum resistance under stretch conduction while maintaining the smallest dimensions. Some of these traces can constitute power lines that provide electrical power to the bio-sensing electronics dispersed all over the garment. In order to mitigate the excessive path resistance, increase due to stretching, the signal monitor 125 may boost the voltage from one bio-sensing node to the other. The boosting is decided by software based on need; i.e. whether the voltage has gone below a threshold. These webs of connectivity can carry high speed digital signals implementing a communication protocol for handling the data transport from the data collection sites, i.e., the electronic circuits of the sensors, to a gateway that funnel all the data stream to the external data analysis compute system outside the garment. The gateway could be connecting to the outside compute system via wire or wireless means.

Figure 2B:
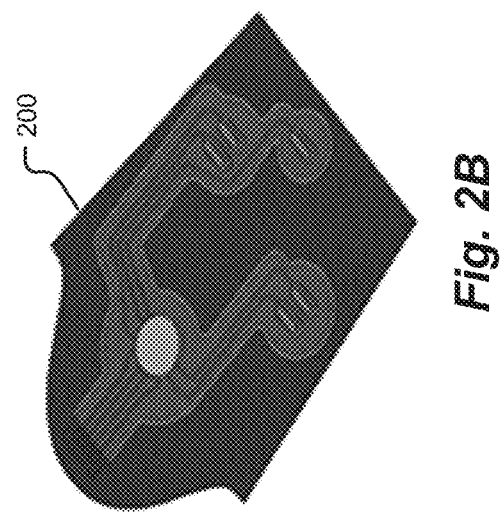

FIGS. 2A and 2B illustrate various views of an exemplary biometric sensor according to one embodiment of the present disclosure. More specifically, FIG. 2A illustrates an exploded view of the exemplary biometric sensor 200 while FIG. 2B illustrates an assembled view of the biometric sensor 200. As illustrated here, the biometric sensor 200 can be constructed of an inner housing 205 and inner seal gasket 210 to prevent dirt and moisture contamination inside of the assembled sensor 200. The inner housing 205 and inner seal gasket can be affixed to a Gilford 215 of pre-cut backing material via a PET stiffener 220. A TPU web 235 can be disposed adjacent to the Gilford 215. The TPU web 235 can have affixed thereto a set of electrodes 230 and can include a number of conductive traces to the electrodes 230. A printed circuit board 225 of the sensor 200 including electronic circuits as known in the art based on the sensor type may be mounted onto the TPU web 235 and a TPU encapsulation layer 240 may be disposed on top of the TPU web 235. Finally, an outer seal gasket 245 and outer housing 250 may be affixed to the sensor 200 to complete enclosure of the printed circuit board 225.

The integration of the sensor 200 with the garment can be carried out in way that the connection between the printed circuit board 225 pinout and the printed connectivity traces on the TPU web 235 can be realized by a mechanical clamping of the inner housing 205, PET stiffener 220, and outer housing 250 as well as other means such as by using conductive adhesive. The integration of the sensor 200 into the garment in this way, together with the inner seal gasket 210 and outer seal gasket 245 provides a tight seal so as to prevent any water or contaminant leakage.

FIGS. 3A and 3B illustrate various views of an exemplary biometric signal monitor according to one embodiment of the present disclosure. More specifically, FIG. 3A illustrates an exploded view of the exemplary biometric signal monitor 300 while FIG. 3B illustrates an assembled view of the biometric signal monitor 300. As illustrated here, the biometric signal monitor 300 can be constructed of an outer housing 305 and outer seal gasket 310 to prevent dirt and moisture contamination inside of the assembled biometric signal monitor 300. The outer housing 305 and outer seal gasket 310 can be affixed to a Gilford 315 of pre-cut backing material via a PET stiffener 320. A TPU web 325 can be disposed adjacent to the Gilford 315. The TPU web 325 can have a number of conductive traces to the connectivity layer described herein. A printed circuit board 330 of the biometric signal monitor 300 including electronic circuits for receiving, processing, and uploading or transmitting biometric information as described herein mounted onto the TPU web 325. Finally, an inner seal gasket 335, inner housing 340, and cover 345 may be affixed to the biometric signal monitor 300 to complete enclosure of the printed circuit board 330.

Figure 4B:
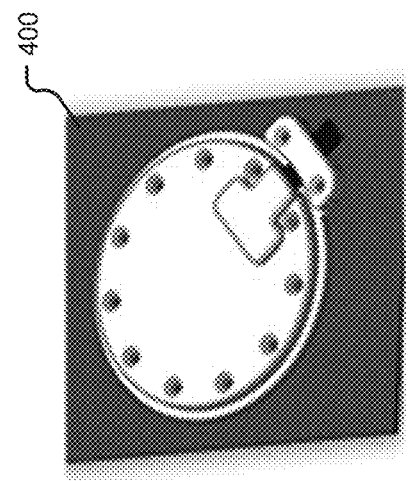
FIGS. 4A and 4B illustrate various views of an exemplary gateway for biometric monitoring according to one embodiment of the present disclosure.
Figure 4A:
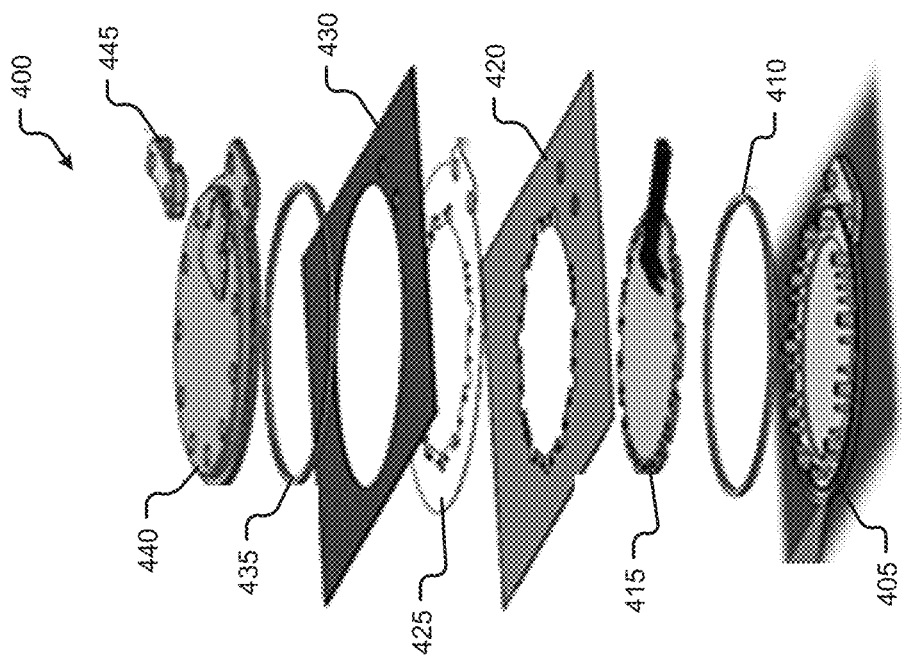

FIGS. 4A and 4B illustrate various views of an exemplary gateway for biometric monitoring according to one embodiment of the present disclosure. More specifically, FIG. 4A illustrates an exploded view of the exemplary gateway 400 while FIG. 4B illustrates an assembled view of the gateway 400. As illustrated here, the gateway 400 can be constructed of an inner housing 405 and inner seal gasket 410 to prevent dirt and moisture contamination inside of the assembled gateway 400. A printed circuit board 415 of the gateway 400 including electronic circuits as known in the art for transmitting biometric information to an external computer may be mounted onto or within the inner housing 405. A TPU web 420 can be disposed adjacent to the inner housing 405 and inner seal gasket 410. A PET stiffener 425 may be disposed adjacent to the TPU web 420 and a Gilford 215 of pre-cut backing material may be disposed next to and affixed to the PET stiffener 425 and TPU web 420. Finally, an outer seal gasket 435 and outer housing 440 may be affixed to the gateway 400 to complete enclosure of the printed circuit board 415. In some cases, a strain relief device 445, such as a spring and/or lever maybe affixed to the outer housing 440.

Figure 5:
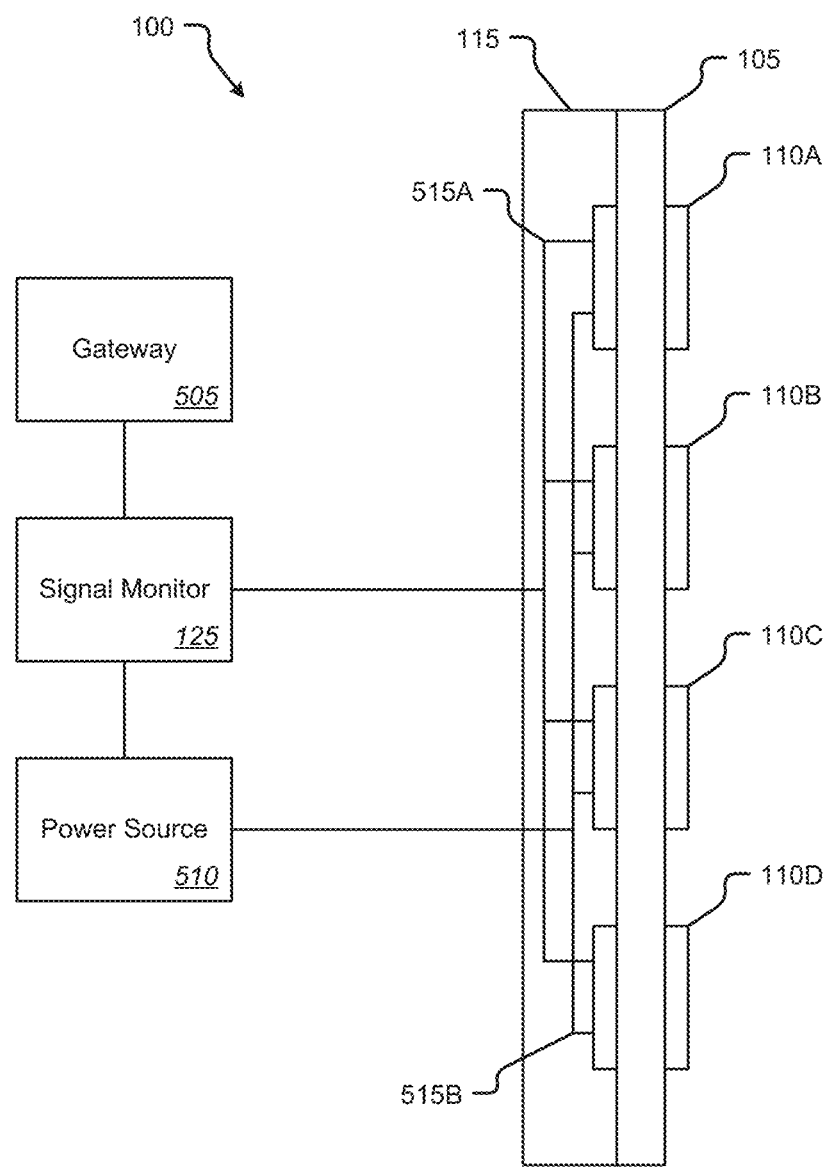
FIG. 5 is a block diagram illustrating exemplary components of a bio-sensing integrated garment according to one embodiment of the present disclosure.

FIG. 5 is a block diagram illustrating exemplary components of a bio-sensing integrated garment according to one embodiment of the present disclosure. As illustrated in this example, a bio-sensing garment 100 for collecting biometric information from a wearer of the garment can comprise a fabric layer 105 forming the garment, a plurality of biometric sensors 110A-110D integrated into the fabric layer 105, and a connectivity layer 115 integrated into the fabric layer 105 as introduced above. For example, the plurality of biometric sensors 110A-110D can comprise any of an electrocardiography (ECG) sensor, a respiration sensor, a PhotoPlethysmoGram (PPG) sensor, a temperature sensor, and/or an electromyography (EMG) sensor. The fabric layer 105 can comprise a multi-ply construction at least in an area of each of the plurality of biometric sensors 110A-110D and can compress each of the biometric sensors 110A-110D to a skin surface of the wearer of the garment 100. In some cases, the fabric layer 105 can form a suit covering substantially all of a torso, arms, and legs of the wearer and the fabric layer can comprise one or more stabilizer portions, e.g., rings, bands, or other structures providing additional compression and/or non-slip surfaces located in each arm sleeve and each leg sleeve to prevent the arm and/or legs sleeves from slipping, riding up or down, rotating, etc.

The connectivity layer 115 can comprise one or more signal conductors 515A coupled with each of the plurality of biometric sensors 110A-110D and one or more power conductors 515B coupled with each of the plurality of biometric sensors. The connectivity layer 115 can further comprise a flexible and stretchable substrate of the garment and the signal conductors 515A and power conductors 515B of the connectivity layer 115 can comprise a plurality of traces of conductive ink printed on the flexible and stretchable substrate. The plurality of traces can comprise one or more straight-shaped traces and one or more meander-shaped traces. Each sensor of the plurality of biometric sensors 110A-110D can be integrated into the garment 100 and can be connected with the connectivity layer 115 by mechanical clamping and/or the use of a conductive adhesive.

The garment 100 can further comprise a power source 510 coupled with each of the power conductors 515B and providing, via the power conductors 515B of the connectivity layer 115, electrical power to each of the plurality of biometric sensors 110A-110D. A signal monitor 125 can be coupled with the connectivity layer 115 and can receive, via the signal conductors 515A of the connectivity layer 115, a signal comprising biometric information from each of the plurality of biometric sensors 110A-110D. A gateway 505 can be coupled with the signal monitor 125. The gateway 505 can receive the biometric information from the signal monitor 125 and provide the biometric information to an external computer system. The signal monitor 125 can also be coupled with the power source 510. In some cases, the signal monitor 125 can compare each received signal comprising biometric information from each of the plurality of biometric sensors 110A-110D to a threshold value corresponding to each sensor. In response to a signal being below the threshold value for the corresponding sensor, a voltage supplied to the corresponding sensor by the power source can be increased.

Figure 6:
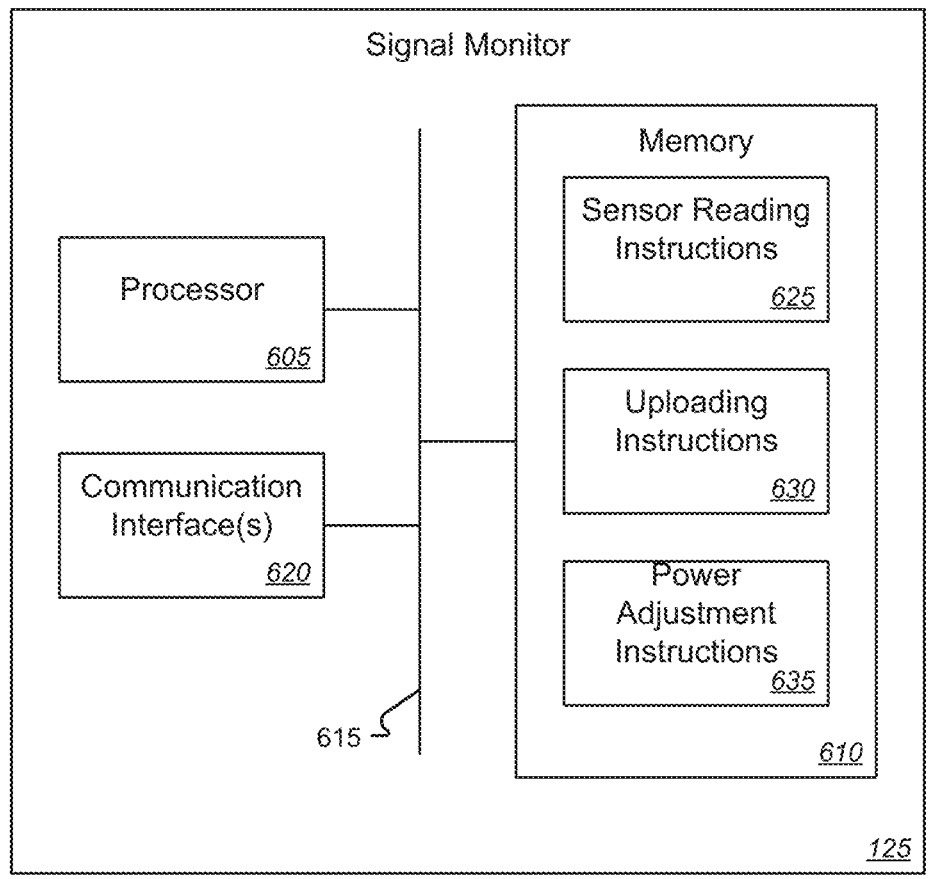
FIG. 6 is a block diagram illustrating exemplary components of a biometric signal monitor according to one embodiment of the present disclosure.

FIG. 6 is a block diagram illustrating exemplary components of a biometric signal monitor according to one embodiment of the present disclosure. As illustrated in this example, a signal monitor 125 of a bio-sensing garment 100 can comprise a processor 605 and a memory 610 coupled with and readably by the processor 605 via a communication bus 615. The memory 610 can store therein a set of instructions which, when executed by the processor 605, causes the processor 605 to collect biometric information from a wearer of the garment 100. For example, the memory 610 can store therein a set of sensor reading instructions 625 which, when executed by the processor 605, can cause the processor 605 to receive biometric information from each of a plurality of biometric sensors 110A-110I integrated into a fabric layer 105 of the garment 100. The plurality of biometric sensors 110A-110I can comprise two or more of an electrocardiography (ECG) sensor, a respiration sensor, a PhotoPlethysmoGram (PPG) sensor, a temperature sensor, and an electromyography (EMG) sensor. The fabric layer 105 can comprise a multi-ply construction at least in an area of each of the plurality of biometric sensors 110A-110I and compresses each of the biometric sensors 110A-110I to a skin surface of the wearer of the garment 100. In some cases, the fabric layer 105 can form a suit covering substantially all of a torso, arms, and legs of the wearer and can comprise one or more stabilizer portions located in each arm sleeve and each leg sleeve.

As described above, the biometric information can be received via a connectivity layer 115 integrated into the fabric layer 105 of the garment 100 and comprising one or more signal conductors 515A coupled with each of the plurality of biometric sensors 110A-110I and one or more power conductors 515B coupled with each of the plurality of biometric sensors 110A-110I. The signal monitor 125 can include one or more communication interfaces 620 providing a connection to the signal conductors 515A of the connectivity layer 115 to allow the processor 605 to receive the biometric information from the plurality of biometric sensors 110A-110I.

The memory 610 can also store a set of uploading instructions 630 which, when executed by the processor 605, can further cause the processor 605 of the signal monitor 125 to provide the received biometric information to an external computer system via a gateway 505 of the bio-sensing garment 100 as described above. In some cases, the memory 610 may also store a set of power adjustment instructions 635 which, when executed by the processor 605, can further cause the processor 605 of the signal monitor 125 to compare each received voltage on the power traces to a threshold value corresponding to each sensor. In response to a voltage being below the threshold value for the corresponding sensor, the power adjustment instructions 635 can cause the processor 605 of the signal monitor 125 to increase a voltage supplied to the corresponding sensor by the power source 510.

Figure 7:
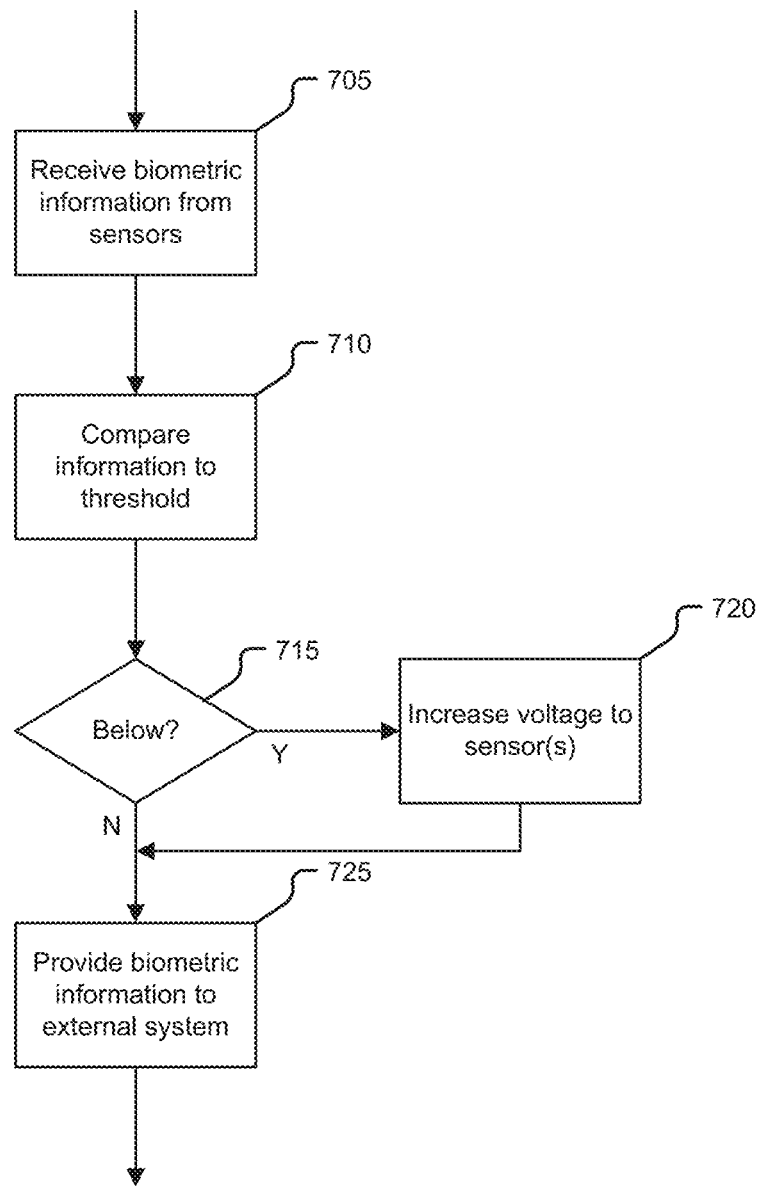
FIG. 7 is a flowchart illustrating an exemplary process for monitoring health of an individual wearing a bio-sensing integrated garment according to one embodiment of the present disclosure.

FIG. 7 is a flowchart illustrating an exemplary process for monitoring health of an individual wearing a bio-sensing integrated garment according to one embodiment of the present disclosure. As illustrated in this example, collecting biometric information from a wearer of a bio-sensing garment can comprise receiving 705, by a signal monitor of the bio-sensing garment, biometric information from each of a plurality of biometric sensors integrated into a fabric layer of the garment. The biometric information can be received 705 via a connectivity layer integrated into the fabric layer of the garment and comprising one or more signal conductors coupled with each of the plurality of biometric sensors and one or more power conductors coupled with each of the plurality of biometric sensors. The plurality of biometric sensors can comprise two or more of an electrocardiography (ECG) sensor, a respiration sensor, a PhotoPlethysmoGram (PPG) sensor, a temperature sensor, and an electromyography (EMG) sensor.

In some cases, each received voltage on the power traces can be compared 710 to a threshold value corresponding to each sensor and a determination 715 can be made as to whether the received voltage is below the threshold. In response to determining 715 a signal being below the threshold value for the corresponding sensor, a voltage supplied to the corresponding sensor by a power source of the bio-sensing garment can be increased 720. The received biometric information can then be provided 725 by the signal monitor of the bio-sensing garment to an external computer system via a gateway of the bio-sensing garment.

To monitor health and muscular activities, a garment 100 such as described herein equipped with bio-sensors 110A-110I could be worn by a person whose health requires a continuous monitoring. Such garment could employ electrodes to track heart, respiration as well as muscular activities. These electrodes should be textile-integratable, capable of reliably picking up the vital or EMG signals from the body, motion-resistant, cleanable, scalable, soft, unperceivable, and minimally interfering with the user's normal activities. The traditional wet-electrodes are not suitable to garment integration as they do not fulfil the above requirements. According to one embodiment, bio-sensors 110A-110I for integration into a garment 100 as described herein can comprise a dry electrode sensor consisting of a conductive pad area, connectivity traces, and a backing.

Figure 8:
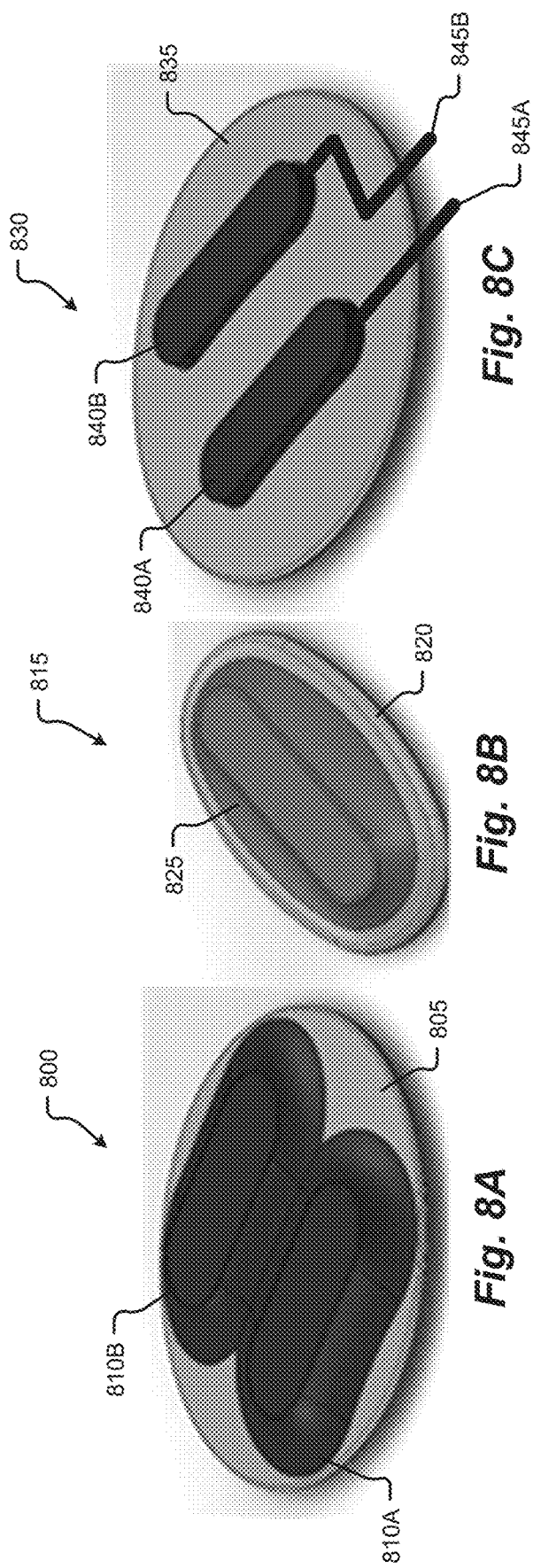
FIGS. 8A-8C illustrate views of different dry electrode sensor constructions according to various embodiments of the present disclosure.

FIGS. 8A-8C illustrate views of different dry electrode sensor constructions according to various embodiments of the present disclosure. More specifically, FIG. 8A illustrates a sensor 800 comprising a backing 805 and two conductive pads 810A and 810B which are the electrodes of the sensor 800. FIG. 8B illustrates a sensor 810 comprising a backing 820 and a single conductive pad 825. FIG. 8C illustrates a sensor 830 comprising a backing 835, two conductive pads 840A and 840B and a set of connectivity traces 845A and 845B.

Regardless of the exact configuration, both the conductive pad area and the connectivity traces can be printed using conductive ink, which is stretchable and washable. The printing can be performed over a substrate that is stretchable and washable such as TPU. To enhance the contact with the skin, the printing of the conductive pad could be textured in different patterns.

Figure 9:
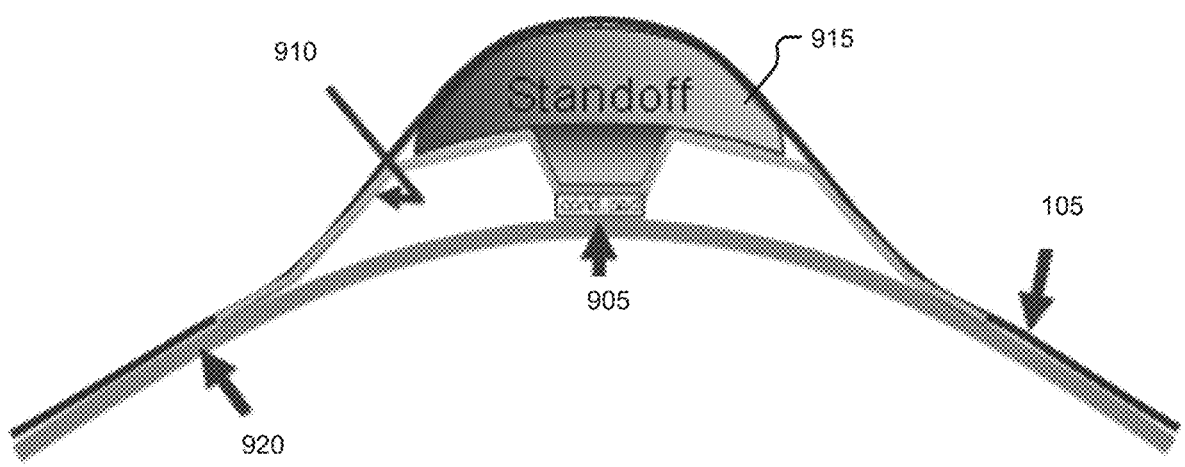
FIG. 9 is a cross-sectional view of a dry electrode sensor according to one embodiment of the present disclosure.

FIG. 9 is a cross-sectional view of a dry electrode sensor according to one embodiment of the present disclosure. As illustrated in this example, a dry electrode bio-sensor 830 can comprise one or more conductive pads 905 comprising electrodes of the dry electrode bio-sensor 830 and one or more connectivity traces 845A and 845B coupled with each of the one or more conductive pads 905. The connectivity traces 845A and 845B can provide electrical connections for one or more of power to the one or more conductive pads 905 or signals comprising biometric information from the one or more conductive pads 905. A backing 910 can be coupled with and can retain the one or more conductive pads 905 and the one or more connectivity traces 845A and 845B. The dry electrode bio-sensor 830 can comprise an electrocardiography (ECG) sensor, a respiration sensor, a PhotoPlethysmoGram (PPG) sensor, a temperature sensor, an electromyography (EMG) sensor, or another biometric sensor.

The one or more conductive pads 905 and the one or more connectivity traces 845A and 845B can be printed in stretchable and washable conductive ink. In some cases, the one or more conductive pads 905 and one or more connectivity traces 845A and 845B can be printed on a stretchable and washable substrate. A surface of each of the one or more conductive pads placed against a wearer's skin 920 when the dry electrode bio-sensor 830 is in use can be textured.

A standoff 915 can be disposed on a side of the backing 910 opposite from the one or more conductive pads 905, the standoff 915 transferring pressure to the one or more conductive pads 905 when the conductive pads 905 are applied to a skin 920 of a wearer of the dry-electrode bio-sensor 830. The standoff 915 can be constructed of a flexible material. The pressure transferred by the standoff 915 to the one or more conductive pads 905 can be applied by a compressive textile, e.g., the fabric layer 105 of the garment 100. The shape of the standoff 915 on a portion adjacent to the compressive textile can have a more curvature than a portion adjacent to the one or more conductive pads 905.

Thus, the electrode has a conductive pad 905 area that interfaces with the skin 920 from which the bio signals are picked up. Note that the conduction pad 905 could be printed on a lamination layer that adheres to the fabric as well as to the standoff 915. The performance of the signal pick-up is a function of the compression exerted on the conductive pad 905 against the skin 920, i.e., the higher the compression the better the signal pick-up. The compression can be attained by having a compressive textile pushing down on the electrode back, i.e., the standoff 915. The compression value applied by the fabric layer 105 is function of the standoff 915 shape.

According to one embodiment, the construction of the standoff 905 could be based on foamy, flexible or rigid materials so as to comply to the skin curvature and thus to provide a more reliable skin contact. The pressure on the conductive pads 905 emanates from the use of compressive textile the wraps around the body part and carries the electrodes. The pressure can be increased by shaping the back of the standoff 915, i.e., the sides that faces the compressive fabric layer 105, so that its curvature is a lot smaller than the body curvature where the electrode is located. The law that governs that the pressure is Laplace's law:

$$P_1 = \frac{T}{R}$$

Where $P_1$ is the pressure applied on the back of the standoff, R is the radius of the curvature of the standoff, T is the tension (N/cm) from the textile due to stretching defined as:

$$T = \frac{F}{W} \cdot \frac{\varepsilon}{\varepsilon_o}$$

Where F is the force applied to a reference sample of width W (cm) that stretched $\varepsilon_0$ (mm), and $\varepsilon$ (mm) is the stretch of the garment wrapped around a part of the body (like arm, leg, or torso).

Also, the area reduction of the area of the back of the standoff with respect to the area of the conductive pad:

$$P_2 = P_1 \frac{A_{standoff\ back}}{A_{conductive\ pad\ area}}$$

The present disclosure, in various aspects, embodiments, and/or configurations, includes components, methods, processes, systems, and/or apparatus substantially as depicted and described herein, including various aspects, embodiments, configurations embodiments, sub-combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A dry electrode bio-sensor comprising:
   one or more conductive pads comprising electrodes of the dry electrode bio-sensor;
   one or more connectivity traces coupled with each of the one or more conductive pads, the one or more connectivity traces providing electrical connections for signals comprising biometric information from the one or more conductive pads;
   a backing coupled with and retaining the one or more conductive pads and the one or more connectivity traces, wherein the backing comprises a stretchable and washable substrate and the one or more conductive pads and the one or more connectivity traces are printed in stretchable and washable conductive ink onto the backing; and
   a standoff disposed between the one or more conductive pads and the backing, the standoff transferring pressure to the one or more conductive pads when the conductive pads are applied to a skin of a wearer of the dry electrode bio-sensor, wherein a shape of the standoff on a portion adjacent to the backing has more curvature than a portion adjacent to the one or more conductive pads and wherein the curvature of the portion of the standoff adjacent to the backing determines a pressure applied by the one or more conductive pads to the skin of the wearer;
   wherein the pressure applied by the one or more conductive pads to the skin of the wearer is determined by Laplace's law, a tension from the stretchable and washable substrate of the backing, and a radius of the curvature of the portion of the standoff adjacent to the backing.

2. The dry electrode bio-sensor of claim 1, wherein a surface of each of the one or more conductive pads placed against a wearer's skin when the dry electrode bio-sensor is in use is textured.

3. The dry electrode bio-sensor of claim 1, wherein the standoff is constructed of a flexible material.

4. The dry electrode bio-sensor of claim 1, wherein the pressure transferred by the standoff to the one or more conductive pads is applied by a compressive textile.

5. The dry electrode bio-sensor of claim 1, wherein the dry electrode bio-sensor comprises an electrocardiography (ECG) sensor.

6. The bio-sensing electrode of claim 1, wherein the dry electrode bio-sensor comprises a respiration sensor.

7. The bio-sensing electrode of claim 1, wherein the dry electrode bio-sensor comprises an electromyography (EMG) sensor.

8. The dry electrode bio-sensor of claim 1, wherein the curvature of the portion of the standoff adjacent to the one or more conductive pads complies with a curvature of the skin of the wearer.

9. The dry electrode of claim 1, wherein the pressure applied by the one or more conductive pads to the skin of the wearer is further determined by a ratio of an area of the portion of the standoff adjacent to the backing to an area of the portion of the standoff adjacent to the one or more conductive pads.

10. A bio-sensing garment for collecting biometric information from a wearer of the garment, the garment comprising:
   a fabric layer forming the garment;
   a plurality of dry electrode bio-sensors integrated into the fabric layer, each dry-electrode bio-sensor comprising:
      one or more conductive pads comprising electrodes of the dry electrode bio-sensor,
      one or more connectivity traces coupled with each of the one or more conductive pads, the one or more connectivity traces providing electrical connections for one or more of signals comprising biometric information from the one or more conductive pads,
      a backing coupled with and retaining the one or more conductive pads and the one or more connectivity traces, wherein the backing comprises a stretchable and washable substrate and the one or more conductive pads and the one or more connectivity traces are printed in stretchable and washable conductive ink onto the backing, and
      a standoff disposed between the one or more conductive pads and the backing, the standoff transferring pressure to the one or more conductive pads when the conductive pads are applied to a skin of a wearer of the dry-electrode bio-sensor, wherein a shape of the standoff on a portion adjacent to the backing has more curvature than a portion adjacent to the one or more conductive pads and wherein the curvature of the portion of the standoff adjacent to the backing determines a pressure applied by the one or more conductive pads to the skin of the wearer; wherein the pressure applied by the one or more conductive pads to the skin of the wearer is determined by Laplace's law, a tension from the stretchable and washable substrate of the backing, and a radius of the curvature of the portion of the standoff adjacent to the backing;
   a connectivity layer integrated into the fabric layer and comprising one or more signal conductors coupled with one or more the connectivity traces of each dry electrode bio-sensors;
   a power source coupled with each of a plurality of power conductors and providing, via the plurality of power conductors, electrical power to each of the plurality of dry electrode bio-sensors;
   a signal monitor coupled with the connectivity layer and receiving, via the signal conductors of the connectivity layer, a signal comprising biometric information from each of the plurality of dry electrode bio-sensors; and
   a gateway coupled with the signal monitor, the gateway receiving the biometric information from the signal monitor and providing the biometric information to an external computer system.

11. The bio-sensing garment of claim 10, wherein a surface of each of the one or more conductive pads placed against a wearer's skin when the dry electrode bio-sensor is in use is textured.

12. The bio-sensing garment of claim 10, wherein the standoff is constructed of a flexible material.

13. The bio-sensing garment of claim 10, wherein the pressure transferred by the standoff to the one or more conductive pads is applied by the fabric layer.

14. The bio-sensing garment of claim 10, wherein the dry electrode bio-sensor comprises an electrocardiography (ECG) sensor, a respiration sensor, or an electromyography (EMG) sensor.

15. The bio-sensing garment of claim 10, wherein the curvature of the portion of the standoff adjacent to the one or more conductive pads complies with a curvature of the skin of the wearer.

16. The bio-sensing garment of claim 10, wherein the pressure applied by the one or more conductive pads to the skin of the wearer is further determined by a ratio of an area of the portion of the standoff adjacent to the backing to an area of the portion of the standoff adjacent to the one or more conductive pads.

* * * * *